United States Patent [19]

Kakimoto et al.

[11] Patent Number: 4,720,564

[45] Date of Patent: Jan. 19, 1988

[54] ANTIOXIDANT ORGANOGERMANIUM COMPOUND

[75] Inventors: Norihiro Kakimoto, Tokyo; Mitsuo Namiki; Toshihiko Osawa, both of Aichi; Kohei Miyao, Tokyo, all of Japan

[73] Assignee: Asai Germanium Research Institute, Tokyo, Japan

[21] Appl. No.: 726,248

[22] Filed: Apr. 23, 1985

[30] Foreign Application Priority Data

Apr. 25, 1984 [JP] Japan ................ 59-81921

[51] Int. Cl.$^4$ ............................................. C07F 7/30
[52] U.S. Cl. ..................................................... 556/83
[58] Field of Search .......................................... 556/83

[56] References Cited

U.S. PATENT DOCUMENTS

| | | | |
|---|---|---|---|
| 3,689,516 | 9/1972 | Asai et al. | 556/83 |
| 3,812,167 | 5/1974 | Pahk | 556/83 |
| 4,066,678 | 1/1978 | Sato et al. | 556/83 |
| 4,271,084 | 6/1981 | Ishikawa et al. | 556/83 |
| 4,508,654 | 4/1985 | Chang et al. | 556/83 |
| 4,579,961 | 4/1986 | Kakimoto | 556/83 |

FOREIGN PATENT DOCUMENTS

| | | | |
|---|---|---|---|
| 56-032485 | 4/1981 | Japan . | |
| 57-203090 | 12/1982 | Japan . | |
| 036686 | 2/1984 | Japan | 260/429 R |

*Primary Examiner*—Helen M. S. Sneed
*Attorney, Agent, or Firm*—Burns, Doane, Swecker & Mathis

[57] ABSTRACT

A new synthetic antioxidant comprising an organogermanium compound represented by the formula:

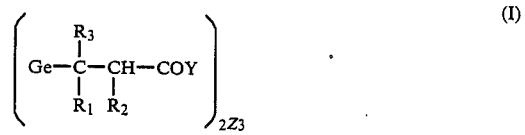

wherein $R_1$, $R_2$ and $R_3$ are one of a hydrogen atom, a substituted or unsubstituted phenyl group or an alkyl group, Y is a hydroxyl or amino group and Z is an oxygen or sulfur atom, is particularly effective in inhibiting auto-oxidation in living organisms.

1 Claim, 3 Drawing Figures

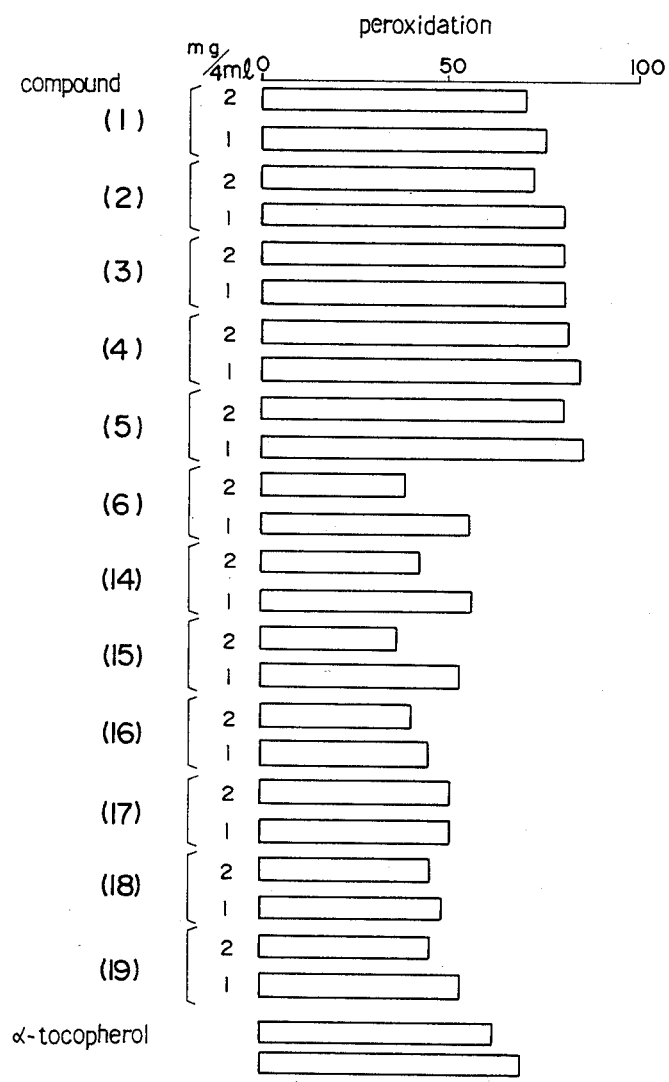

ANTIOXIDANT ORGANOGERMANIUM COMPOUND

BACKGROUND OF THE INVENTION

1. Field of the Invention

The present invention relates to a new type of antioxidant containing an organogermanium compound as a principal ingredient.

2. Description of the Prior Art

Oxygen is an indispensable substance not only for human beings but also for all aerobic organisms, but it is well known that oxygen causes various undesired phenomena. For example, fat or oil contained in food is auto-oxidized with oxygen in air to result not only in a decrease in the quality as a favorite food and the nutritive value, but also in the generation of toxic substances by the formation of peroxides. Further, in living organisms, the formation of peroxides is recently noted as a cause of aging, cancero-genesis or the like.

That is to say, it is believed that an unsaturated fatty acid, for example, polyunsaturated fatty acid which is particularly important as phospholipids or the like and is an indispensable component in food as an essential fatty acid, is subjected to auto-oxidation with free radical of oxygen or oxidant, which is a free radical chain reaction, to form peroxylipids called "hydroperoxide", and this hydroperoxide and products formed by the oxidative destruction of endo-peroxide generated during the auto-oxidation, such as malonaldehyde, act on DNA, RNA, protein or membrane tissue, thus taking part in the above diseases.

Adriamycin contained in anthracycline antineo-plastic agent which is one of chemotherapeutic agents used in the medical treatment of carcinoma is known to have a particularly wide antineoplastic spectrum. However, it has been reported that adriamycin exhibits some side effects. Furthermore, it has been proposed that cardiotoxicity which is one of the side effects is caused by the peroxidation of lipid with superoxide anion free radical ($O_2^-$), hydroxyl free radical ($\dot{O}H$), singlet oxygen ($'O_2^-$) or the like which are derived from the quinone structure present in the chemical structure of adriamycin (Edward G. Mimnaugh et al., the Journal of Pharmacology and Experimental Therapeutics, Vol. 226, No. 3,806 (1983)).

Many efforts have been made to inhibit the above auto-oxidation. Presently, synthesized phenolic antioxidants such as butylhydroxyanisole (BHA) or butylhydroxytoluene (BHT) and natural antioxidants such as tocopherol are known and the former is widely used.

However, these synthetic antioxidants have disadvantages with respect to safety. For example, BHA tends to cause disturbances in a liver. On the contrary, natural antioxidant are known to have disadvantages with respect to the source of supply, effects and cost. Therefore, some of the inventors of the present invention had investigated in order to find effective natural antioxidant other than tocopherol and succeeded in developing an effective, safe and natural antioxidant containing n-tritriacontane-16,18-dione which is contained in leaf wax of eucalyptus, as a principal ingredient (Japanese Patent Publication No. 57-26744). Further, it is also desired that effective, safe and synthetic antioxidants are developed.

SUMMARY OF THE INVENTION

The present invention has been made under these circumstances and is characterized by containing an organogermanium compound represented by the general formula:

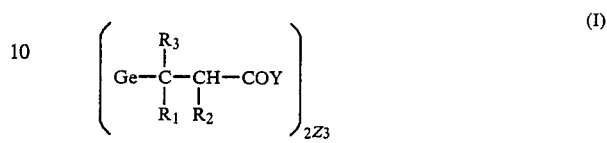

wherein $R_1$, $R_2$ and $R_3$ are one of a hydrogen atom, a substituted or unsubstituted phenyl group or an alkyl group, Y is a hydroxyl or amino group and Z is an oxygen or sulfur atom.

BRIEF DESCRIPTION OF THE DRAWINGS

The attached drawings show the antioxidizing ability of the antioxidants according to the present invention, wherein.

DETAILED DESCRIPTION OF PREFERRED EMBODIMENTS

Figure 1:
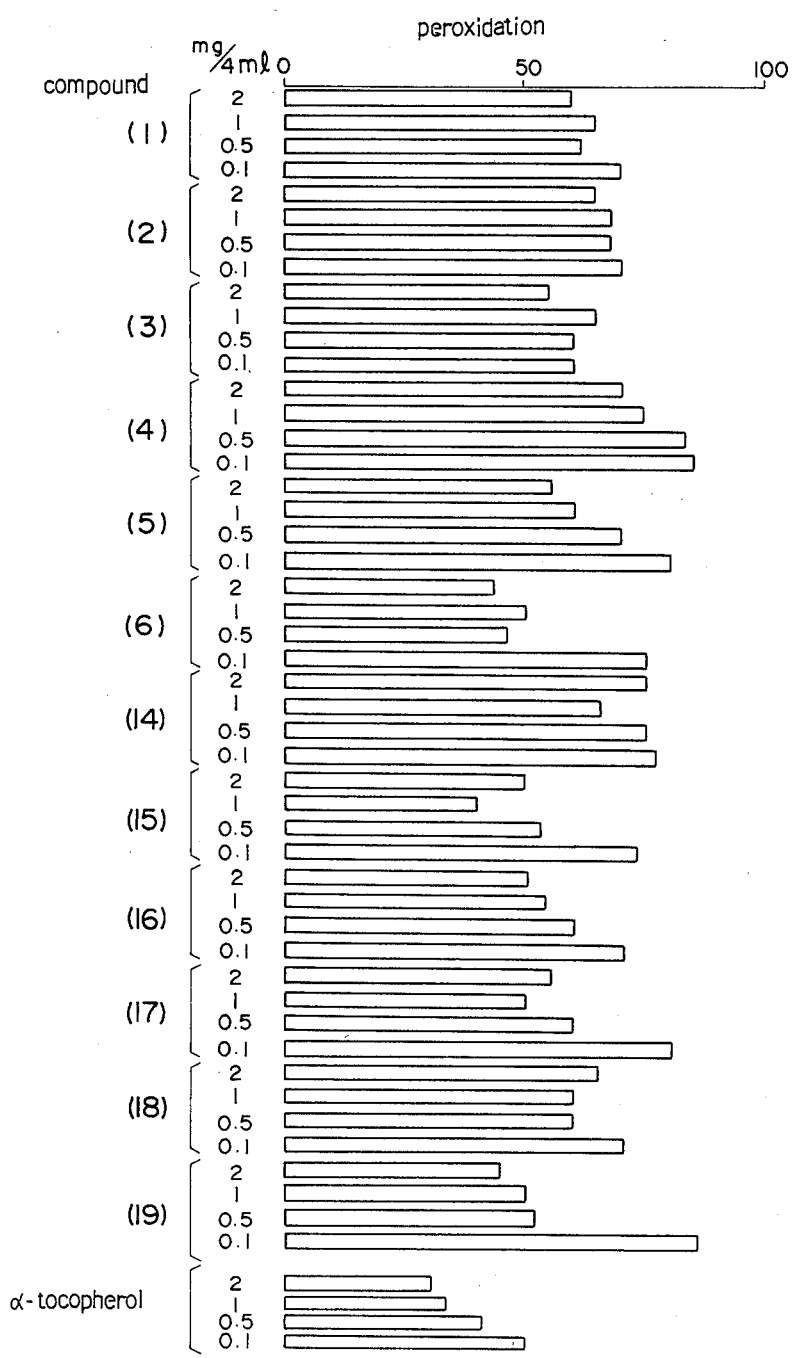
FIG. 1 shows the case where rabbit red blood cell ghost is used.

The antioxidant of the present invention contains an organogermanium compound represented by the general formula (I). In this formula, substituents $R_1$, $R_2$ and $R_3$ are one of a hydrogen atom, a substituted or unsubstituted phenyl group or an alkyl group such as methyl or ethyl, and a substituent Y is a hydroxyl or amino group.

A substituent Z stands for an oxygen or sulfur atom. Accordingly, when Z is O, the organogermanium compound represented by the general formula (I) is a sesquioxide comprising the main structures and oxygen atoms which are bonded with each other in a ratio of 2:3, while, when Z is S, it is a sesquisulfide comprising the main structures and sulfur atoms which are bonded with each other in a ratio of 2:3.

The organogermanium compounds to be used in the present invention are expendiently represented by the general formula (I) according to a usual practice. However, the organogermanium compound is a large molecule comprising the main structures and oxygen or sulfur atoms which are bonded with each other in a ratio of 2:3, and therefore the general formula (I) does not represent the structure of this organogermanium compound exactly. Accordingly, the above organogermanium compound can be also represented by the general formula:

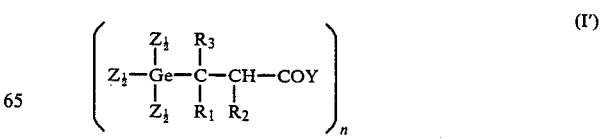

or by the general formula:

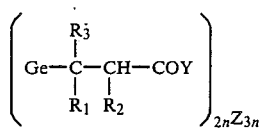

$$\left( \begin{array}{c} R_3 \\ | \\ Ge-C-CH-COY \\ | \phantom{xx} | \\ R_1 \phantom{xx} R_2 \end{array} \right)_{2n}Z_{3n} \qquad (I'')$$

The above organogermanium compounds can be prepared by various methods.

For example, the sesquioxide compound represented by the general formula (I) wherein Z is an oxygen atom, and Y is a hydroxyl group can be prepared by a process which comprises reacting trichlorogermane $$Cl_3GeH \qquad (II)$$

with an acrylic acid derivative $$\begin{array}{c} R_3 \\ | \\ C=C-COOH \\ | \phantom{xx} | \\ R_1 \phantom{xx} R_2 \end{array} \qquad (III)$$

to obtain a derivative of trichlorogermylpropionic acid $$\begin{array}{c} R_3 \\ | \\ Cl_3Ge-C-CH-COOH \\ | \phantom{xx} | \\ R_1 \phantom{xx} R_2 \end{array} \qquad (IV)$$

and hydrolyzing it, or by a process which comprises reacting the above trichlorogermane (II) with an acrylonitrile derivative $$\begin{array}{c} R_3 \\ | \\ C=C-CN \\ | \phantom{xx} | \\ R_1 \phantom{xx} R_2 \end{array} \qquad (III')$$

to obtain a trichlorogermylpropionitrile derivative $$\begin{array}{c} R_3 \\ | \\ Cl_3Ge-C-CH-CN \\ | \phantom{xx} | \\ R_1 \phantom{xx} R_2 \end{array} \qquad (IV')$$

and hydrolyzing it.

The sesquisulfide compound represented by the general formula (I) wherein Z is a sulfur atom and Y is a hydroxyl group can be obtained by a process which comprises dissolving the above trichlorogermylpropionic acid derivative (IV) in an anhydrous solvent and passing dry hydrogen sulfide through the solution in the presence of anhydrous pyridine.

In any case, the compound represented by the general formula (I) wherein Y is $NH_2$, can be obtained, for example, by a process which comprises reacting a trichlorogermylpropionic acid derivative (IV) with a halogenating agent to form the corresponding acyl halide and treating the halide with ammonia, followed either by hydrolyzing the product or by passing dry hydrogen sulfide therethrough.

In the preparation of the sesquioxide or sesquisulfide, it is believed that $ZH_2$ is eliminated intermolecularly from an intermediate (V)

$$\begin{array}{c} ZH \phantom{xx} R_3 \\ | \phantom{xx} | \\ HZ-Ge-C-CH-COOH \\ | \phantom{xx} | \phantom{xx} | \\ ZH \phantom{xx} R_1 \phantom{xx} R_2 \end{array} \qquad (V)$$

which has first been formed to obtain the organogermanium compound represented by the general formula (I).

The organogermanium compound synthesized as above was examined for antioxidizing ability in living organism by mainly using a system similar to that in vitro.

More particularly, peroxidation due to t-butylhydroperoxide which is a kind of peroxides was measured by using a system containing red blood cell ghost (fragments of cell membrane) and peroxidation depending on NADPH due to ADP-$Fe^{3+}$, oxygen free radical, hydrogen peroxide and hydroxyl free radical using P-450 system of rat liver microsome and peroxidation due to the above adriamycin were measured. As a result of these measurements, it has been found that the antioxidant of the present invention exhibits an excellent antioxidizing ability like that of the above described tocopherol.

Now, experimental examples of the present invention will be described.

EXPERIMENTAL EXAMPLE 1

Synthesis of the organogermanium compound represented by the general formula (I)

① Sesquioxide of 2-methyl-3-germylpropionic acid (1).

84.7 ml (0.1 mol) of methacrylic acid was added dropwise over 5 minutes to 18 g (0.1 mol) of crude trichlorogermane which had been cooled to 5° C. in an ice bath. The mixture was stirred at the same temperature for one hour and then at room temperature for 1.5 hour. The precipitated crystal was filtered by suction, washed with 10ml of n-hexane which had been dried over potassium chloride for four times, dried by suction and kept in a desiccator containing phosphorus pentoxide at 65° C. for one hour with reducing the pressure by a vacuum pump which uses potassium hydroxide containing trap to obtain 17.03 g of crystalline 2-methyl-3-(trichlorogermyl)propionic acid:

melting point 54°~55° C.

IR spectrum (KBr, $cm^{-1}$): 2950~3600, 1690, 1265, 580, 550, 405,

NMR spectrum ($CDCl_3$, δ): 1.46 (3H, d), 2.33 (2H, dd), 3.03 (1H, q), 10.13 (1H, s).

elemental analysis: calculated: C 18.05, H 2.63, Cl 40.00, found: C 18.12, H 2.70, Cl 39.97.

10 ml of pure water was added to 2 g (0.0075 mol) of crystalline 2-methyl-3-(trichlorogermyl)propionic acid obtained according to the above procedure. The temperature of the solution rose to 25° C., and the compound was completely dissolved. After 2 minutes, the solution became turbid and crystal began to precipitate. The solution was heated to 85° C. and maintained at that temperature for one hour to precipitate the crystal completely. The crystal was filtered, washed with 10 ml of pure water, 10 ml of 99.5% ethanol and then 10 ml of ether and dried by suction to obtain 0.638 g of crystalline sesquioxide of 2-methyl-3-germylpropionic acid (yield: 86.3%).

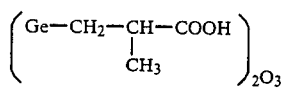

sesquioxide of 2-methyl-3-germylpropionic acid (1).

IR spectrum (KBr, cm$^{-1}$): 3420, 1705, 1245, 900, 802.

NMR spectrum (D$_2$O, δ): 1.30 (3H, d), 1.68 (2H, dd), 2.93 (1H, m).

elemental analysis: calculated: C 26.16, H 3.84, found: C 25.52, H 4.08.

② Sesquioxide of 2-methyl-3-germylpropionamide (7)

100 ml of thionyl chloride was added to 26.6 g (0.1 mol) of 2-methyl-3-(trichlorogermyl)propionic acid prepared by the above process ①. The mixture was heated under reflux for 10 hours and distilled under a reduced pressure to remove excess thionyl chloride. 25.1 g of the corresponding acid chloride was obtained as a colorless transparent portion having a boiling point of 101° to 101.5° C./6 mmHg (yield: 88%).

5.69 g (0.02 mol) of this chloride was dissolved in 150 ml of anhydrous benzene. Dry ammonia was introduced into the solution under cooling with an ice bath for one hour, followed by the introduction of gaseous hydrogen chloride for one hour. 100 ml of methyl acetate was added to the solution and the mixture was stirred and filtered. The filtrate was distilled and the obtained residue was recrystallized from a mixture of acetone and benzene (1:2) to obtain 5 g of the corresponding amide (yield: 79.8%).

5.70 g (0.02 mol) of the resulting amide was treated according to an ordinary method to hydrolyze only the germanium-chloride bonds. 3.01 g of the objective compound having the following characteristics was obtained (yield: 79.8%).

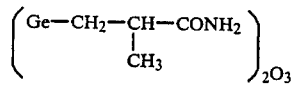

sesquioxide of 2-methyl-3-germylpropionamide (7)

IR spectrum (KBr, cm$^{-1}$) 1660, 900, 800.

elemental analysis: calculated Ge: 39.73 C: 26.30 H: 4.41 N: 7.67, found Ge: 39.52 C: 26.37 H: 4.39 N: 7.61.

DTA: endothermic peak at 246° C., exothermic peak at 315° C.

Examples of the compounds represented by the general formula (I) wherein Z is 0 include the following compounds as well as the above compounds (1) and (7). The following compounds can be prepared by the method similar to that described above and exhibited the characteristics as shown in Table 1.

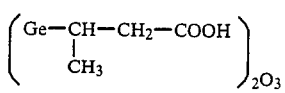 (2)

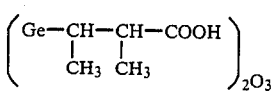 (3)

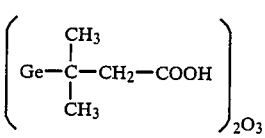 (4)

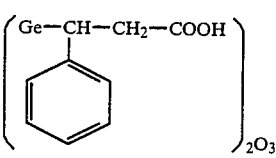 (5)

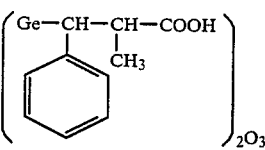 (6)

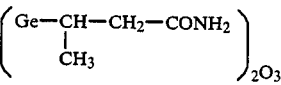 (8)

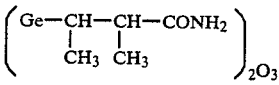 (9)

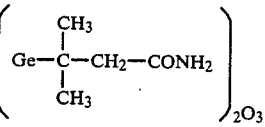 (10)

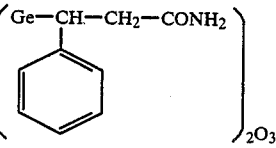 (11)

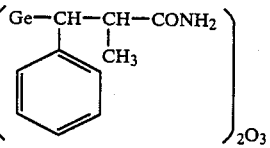 (12)

TABLE (1)

| Compound | Elemental analysis calculated/found | | | Melting point (°C.) | IR (KBr, cm$^{-1}$) | NMR (δ) (solvent) | | Yield (%) |
| --- | --- | --- | --- | --- | --- | --- | --- | --- |
| | Ge | C | H | | | | | |
| (2) | 39.52/39.45 | 26.16/25.73 | 3.84/4.02 | 184° C. (dec) | 1700 900 800 | D$_2$O | 1.23 (3H, d) 2.05 (1H, m) 2.67 (2H, dd) | 98.0 |
| (3) | 36.72/36.60 | 30.37/30.39 | 4.59/4.58 | 228° C. (dec) | 1715 880 | D$_2$O | 1.20 (3H, d) 1.30 (3H, d) | 84.7 |

TABLE (1)-continued

| | Characteristics | | | | | | |
|---|---|---|---|---|---|---|---|
| | Elemental analysis calculated/found | | | Melting point | IR | NMR (δ) | Yield |
| Compound | Ge | C | H | (°C.) | (KBr, cm$^{-1}$) | (solvent) | (%) |
| (4) | 36.72/36.66 | 30.37/30.37 | 4.59/4.55 | 230° C. (dec) | 1690 895 795 | D$_2$O | 2.10 (1H, m) 2.90 (1H, m) 1.30 (6H, s) 2.55 (2H, s) | 65.8 |
| (5) | 29.54/29.55 | 43.99/44.01 | 3.69/3.61 | 200° C. (dec) | 1710 880 700 | D$_2$O | 3.00 (2H, s) 3.35 (1H, t) 7.35 (5H, m) | 84.5 |
| (6) | 27.94/27.99 | 46.23/46.21 | 4.27/4.27 | 200° C. (dec) | 1710 880 700 | D$_2$O | 1.15 (3H, m) 3.20 (2H, d) 7.30 (5H, m) | 86.6 |

③ Sesquisulfide of 2-methyl-3-germylpropionic acid (15).

5.3 g (0.02 mol) of 2-methyl-3-(trichlorogermyl)propionic acid was dissolved in 100 ml of anhydrous benzene. 5.2 g (0.066 mol) of anhydrous pyridine was added to the solution under cooling with an ice bath, followed by stirring. Dry hydrogen sulfide was introduced into the mixture for one hour. The benzene was removed and the residue was dissolved in 30 ml of methanol. The solution was added to 100 ml of chilled water. The mixture was stirred for 2 hours to precipitate crystal. The crystal was recrystallized from a mixture of methanol and water (1:1) to obtain 3.9 g of crystalline sesquisulfide of 2-methyl-3-germyl propionic acid (yield: 93%).

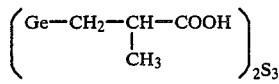

sesquisulfide of 2-methyl-3-germylpropionic acid (15)

IR spectrum (KBr, cm$^{-1}$): 3450, 1705, 1245, 425.

NMR spectrum (CD$_3$OD, δ): 1.38 (3H, d), 2.03 (2H, m), 2.94 (1H, m).

elemental analysis: calculated: Ge 34.94, C 23.13, H 3.40, S 23.15, found: Ge 35.79, C 23.39, H 3.45, S 22.96.

④ Sesquisulfide of 3-phenyl-3-germylpropionic acid (18).

16.4 g (0.05 mol) of 3-phenyl-3-(trichlorogermyl)propionic acid was dissolved in 200 ml of anhydrous acetone. 12.6 g (0.16 mol) of anhydrous pyridine was added to the solution under cooling with an ice bath, followed by stirring. Dry hydrogen sulfide was introduced into the mixture for one hour. The acetone was removed and the residue was dissolved in 50 ml of ethanol. The solution was added to 400 ml of water to precipitate the crystal. The crystal was recrystallized from a mixture of methyl acetate and benzene (1:3) to obtain 12.7 g of crystalline sesquisulfide of 3-phenyl-3-germylpropionic acid.

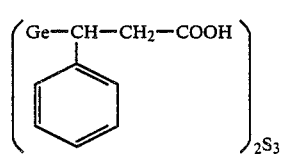

sesquisulfide of 3-phenyl-3-germylpropionic acid (18).

IR spectrum (KBr, cm$^{-1}$): 3450, 1710, 1600, 1410, 1230, 700, 425.

NMR spectrum (acetone-d$_6$, δ): 3.05 (2H, d), 3.62 (1H, t), 7.23 (5H, m).

elemental analysis: calculated: Ge 26.90, C 40.06, H 3.36, S 17.82, found: Ge 26.92, C 39.83, H 3.41, S 17.64.

⑤ Sesquisulfide of 2-methyl-3-germyl-3-methylpropionamide (23).

28.0 g (0.1 mol) of 2-methyl-3-(trichlorogermyl)butanoic acid was treated with 100 ml of thionyl chloride. The reaction mixture was distilled under a reduced pressure to obtain 27.0 g of 2-methyl-3-(trichlorogermyl)butanoyl chloride as a pale yellow portion having a boiling point of 99° to 100° C./6 mmHg (yield: 90.4%).

5.8 g (0.02 mol) of this chloride was dissolved in 50 ml of anhydrous benzene. Dry ammonia was introduced into the solution under cooling with an ice bath for one hour, followed by the introduction of gaseous hydrogen chloride for one hour. 100 ml of methyl acetate was added and the mixture was stirred and filtered. The filtrate was distilled and the residue was recrystallized from a mixture of acetone and benzene (1:2) to obtain 4.1 g of 2-methyl-3-(trichlorogermyl)butanamide (yield: 76.0%).

10.8 g (0.04 mol) of the above 2-methyl-3-(trichlorogermyl)butanamide was dissolved in 200 ml of anhydrous benzene. 9.5 g (0.12 mol) of anhydrous pyridine was added to the solution, followed by stirring. Dry gaseous hydrogen sulfide was passed through the solution for one hour. The precipitated compound was separated and purified either by the recrystallization from hydrous acetone or by the isolation using molecular sieves such as Sephadex LH-20 (trademark) and methanol as a developer to obtain 7.8 g of the objective compound (yield: 88.3%).

sesquisulfide of 2-methyl-3-germyl-3-methylpropionamide (23).

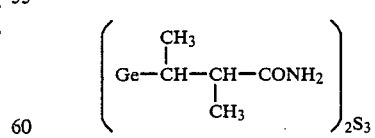

melting point: 205° C. (dec.)

IR (KBr, cm$^{-1}$): 3400, 3200, 2960, 1660, 1460, 1400, 780, 570, 420.

NMR (CD$_3$OD, δ): 1.30 (3H, d, CO—CH—C$\underline{H}$), 1.38 (3H, d, Ge—CH—C$\underline{H}$), 2.14 (1H, m, Ge—C$\underline{H}$), 2.27 (1H, m, CO—C$\underline{H}$), 2.70 (2H, d, N$\underline{H}_2$).

elemental anaysis:

|  | Ge | C | H | N | S |
|---|---|---|---|---|---|
| calculated: | 32.87 | 27.20 | 4.56 | 6.34 | 21.87 |
| found: | 32.59 | 27.37 | 4.43 | 6.25 | 21.56 |

Examples of the compounds represented by the general formula (I) wherein Z is S include the following compounds as well as the above compounds (15), (18) and (23). The following compounds were prepared by the methods similar to that described above and exhibited the characteristics as shown in Table 2-1 and -2.

(GeCH$_2$CH$_2$COOH)$_2$S$_3$ (13)

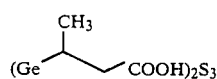 (14)

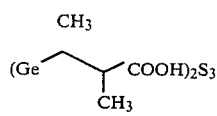 (16)

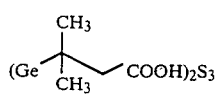 (17)

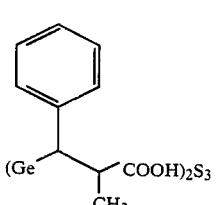 (19)

(GeCH$_2$CH$_2$CONH$_2$)$_2$S$_3$ (20)

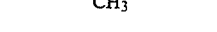 (21)

 (22)

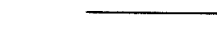 (24)

 (25)

 (26)

TABLE 2 - 1

| | Characteristics | | | | | | | | |
|---|---|---|---|---|---|---|---|---|---|
| | Elemental analysis calculated/found | | | | Melting point | IR | NMR (δ) | | Yield |
| Compound | Ge | C | H | S | (°C.) | (KBr, cm$^{-1}$) | (solvent) | | (%) |
| (14) | 34.92/35.21 | 23.13/23.17 | 3.40/3.39 | 23.15/23.34 | 185° C. (dec) | 1705 425 | CD$_3$OD | 1.36 (3H, d) 2.08~2.95 (3H, m) | 57.7 |
| (16) | 32.73/32.53 | 27.07/27.26 | 4.09/4.10 | 21.68/21.57 | 200° C. (dec) | 1700 400 | CD$_3$OD | 1.33 (3H, d) 1.40 (3H, d) 2.18 (1H, m) 2.60 (1H, m) | 92.4 |
| (17) | 32.73/32.64 | 27.07/27.17 | 4.09/4.14 | 21.68/21.54 | 190° C. (dec) | 1700 425 | CD$_3$OD | 1.46 (6H, s) 2.60 (2H, s) | 80.3 |
| (19) | 25.57/25.49 | 42.31/42.33 | 3.91/3.90 | 16.94/16.99 | 190° C. (dec) | 1705 700 425 | acetone –d$_6$ | 1.43 (3H, m) 3.27 (2H, m) 7.17 (5H, s) | 86.0 |

TABLE 2 - 2

| | Characteristics | | | | | | | | |
|---|---|---|---|---|---|---|---|---|---|
| | Elemental analysis calculated/found | | | | | Melting point | IR | NMR (δ) | Yield |
| Compound | Ge | C | H | N | S | (°C.) | (KBr, cm$^{-1}$) | (Solvent) | (%) |
| (14) | 32.87/32.96 | 27.20/27.14 | 4.56/4.68 | 6.34/6.11 | 21.78/21.53 | 230° C. (dec) | 3400, 3200 2960, 1660 1460, 1120 420 | CD$_3$OD 1.26 (6H, s) 2.86 (2H, s) | 76.5 |
| (16) | 27.00/27.26 | 40.20/40.34 | 3.75/3.93 | 5.21/5.18 | 17.89/17.66 | 210° C. (dec) | 3450, 3350 3200, 1660 1600, 1400 765, 700, 420 | DMF d$_{-6}$ 2.43 (1H, t) 3.05 (2H, d) 7.23 (5H, m) | 81.8 |
| (17) | 25.66/25.87 | 42.46/42.49 | 4.27/4.33 | 4.95/4.70 | 17.00/16.86 | 215° C. (dec) | 3450, 3350 3200, 1660 1455, 1400 700, 420 | | 82.3 |

EXPERIMENTAL EXAMPLE 2

Test of the compound represented by the general formula (I) for antioxidizing ability.

Antioxidation test using an in-vitro system (rabbit red blood cell ghost)

About three times by volume as much isotonic liquid was added to 50~200 ml of commercially available preserved rabbit blood. The mixture was subjected to centifugation three times at 3,500 r.p.m. for 20 minutes. About three times by volume as much 10 mM phosphate buffer was added to the precipitate. The mixture was subjected to centifugation four times at 13,000 r.p.m. for 40 minutes. The obtained precipitate was used as red blood cell ghost. The precipitate was diluted so as to give a suspension containing about 10 mg of protein per 4 ml of the buffer as determined by the Lowry's method. The corresponding amount of the ghost suspension was placed in a test tube. 5 μl of t-butyl hydroperoxide as an oxidation accelerator and an antioxidant of the present invention diluted with dimethyl sulfoxide (DMSO) or distilled water (when the antioxidant is dissolved in DMSO, not more than 50 μl of the solution is preferably used) were added to the test tube, followed by the addition of the above 10 mM phosphate buffer so as to give a total amount of 1 ml. The suspension was shaken at 37° C. for 20 minutes in a thermostatic chamber. 1 ml of a 20% aqueous solution of TCA and 2 ml of a 0.67% aqueous solution of TBA were added to the suspension. The mixture was heated in a boiling water bath for 15 minutes, cooled with water and centrifuged at 3,500 r.p.m. for 15 minutes. The degree of the antioxidizing effect was determined by measuring the absorbance of the supernatant.

The ratio of the value obtained by subtracting the absorbance of the blank using no t-butyl hydroperoxide from that of the control using t-butyl hydroperoxide to the value of the absorbance of the control was calculated and shown by percentage as antioxidation activity.

The results are shown in FIG. 1.

Antioxidation test using an in-vitro system (rat liver microsome)

① The heads of Wistar rats (8 weeks, 180 to 200 g ♂) which had gone without food for one day were cut off and their abdomens were cut to take out livers. The livers were perfused with about 40 ml of a 0.95% chilled solution of sodium chloride to remove blood contained in the livers. 80 ml (per liver of a rat) of a 0.25M chilled solution of sucrose was added to the livers and the mixture was homogenized under cooling with an ice bath and centrifuged at 13,000 r.p.m. for 10 minutes. The supernatant was further centrifuged at 37,500 r.p.m. for one hour. About 20 ml of a 125 mM solution of potassium chloride was added to the precipitate and the resulting mixture was again homogenized to obtain a microsome suspension.

The suspension was diluted so as to give a suspension containing 1.5 mg of protein per 6.5 ml of buffer as measured by the Lowery's method.

The amount corresponding to a protein amount of 1.5 mg of the microsome suspension was placed in a test tube. A proper amount of an antioxidant of the present invention, ADP (400μ, final concentration—the same applies herein-below), NADPH (120 μM) and $FeSO_4 \cdot 7H_2O$ (500 μM) were added to the test tube, followed by the addition of a mixture of 0.1M Trisbuffer (pH 7.4) and 0.15M KCl (1:2) so as to give a total amount of 1.5 ml. The mixture was shaken in a thermostatic chamber at 37° C. for 30 minutes. 3 ml of a 10% solution of TCA and 2 ml of a 0.67% solution of TBA were added to the test tube. The mixture was heated in a boiling water bath for 15 minutes, cooled with water and centrifuged at 3,500 r.p.m. for 10 minutes. The degree of the antioxidizing effect was determined by measuring the absorbance of the supernatant at 532 nm.

The ratio of the value obtained by subtracting the absorbance of the blank without ADP, NADPH nor $FeSO_4 \cdot 7H_2O$ from that of the control with ADP, NADPH and $FeSO_4 \cdot 7H_2O$ to the value of the absorbance of the control was calculated and shown by percentage as an antioxidation activity.

Figure 2:
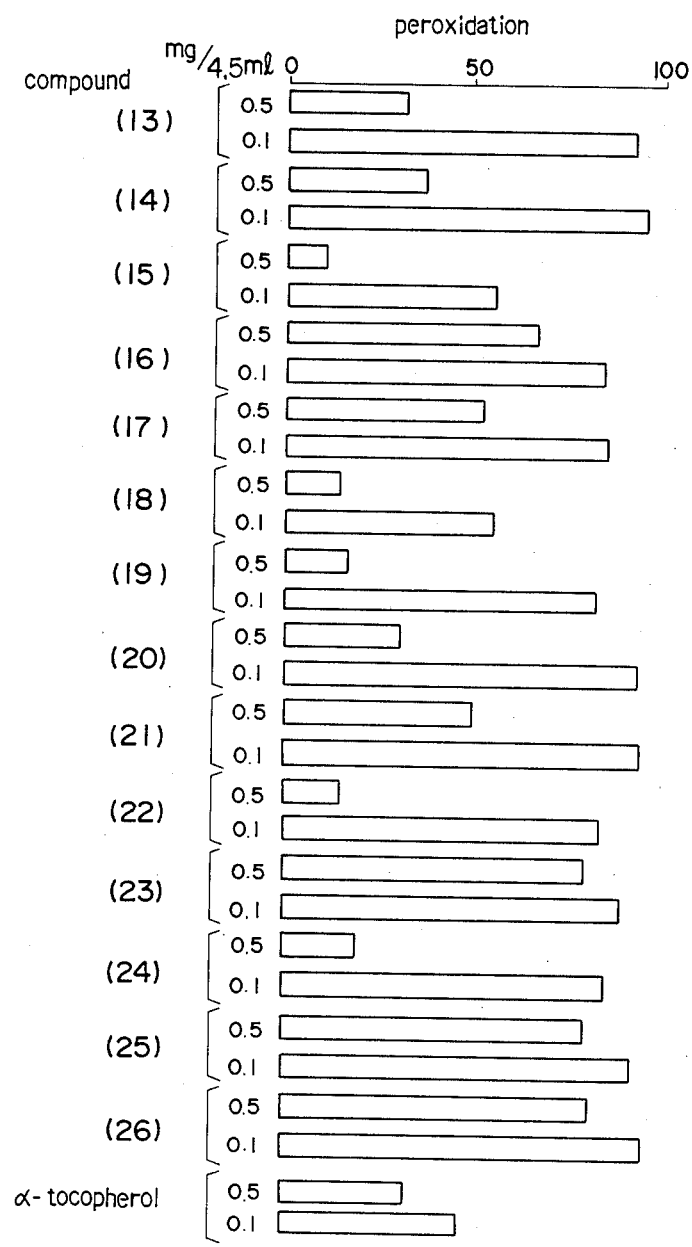
FIG. 2 shows the case where rat liver microsome is used, wherein (a) is the case due to ADP-$Fe^{+3}$, while (b) is the case due to adriamycin.

The results are shown in FIG. 2(a).

② A liver was taken out from a rat whose head had been cut off, homogenized in a 150 mM KCl-150 mM Tris HCl buffer (pH 7.4) and centrifuged at 9,000 G for 3 minutes and then at 105,000 G for one hour to obtain a microsome suspension. The suspension was diluted as described in ① to form a suspension containing 1 mg of protein per 1 ml of buffer as measured by the Lowry's method.

The suspension was placed in a test tube, followed by the addition of a proper amount of an antioxidant of the present invention and such an amount of adriamycin as to give a final concentration of 100 μM. Then, 1.9 mM NADP, 20 mM glucose-6-phosphoric acid, 1.1 I.U./ml glucose-6-phosphoric acid dehydrogenase and 8.6 mM magnesium chloride were added to the test tube each in the form of aqueous solution to give a total amount of 1.75 ml. As described in ①, the solution was treated in a thermostatic chamber and the degree of the antioxidizing effect was determined by measuring the absorbance of the supernatant at 532 nm.

The blank and control were prepared as in ①.

The results are shown in FIG. 2(b).

What is claimed is:

1. An organogermanium compound represented by the general formula:

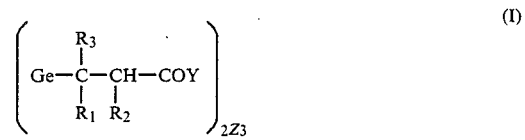

(I)

wherein if Z is a sulfur atom, Y is a hydroxyl or amino group, (i) and at least one of $R_1$, $R_2$ and $R_3$ is a phenyl group and the other two substituents are selected from the group consisting of a hydrogen atom, an alkyl group, and a phenyl group, (ii) at least two of $R_1$, $R_2$ and $R_3$ are phenyl groups and the other substituent is selected from the group consisting of a hydrogen atom, an alkyl group, a phenyl group, or (iii) all three of $R_1$, $R_2$ and $R_3$ are alkyl groups;

wherein if Z is an oxygen atom and Y is an amino group, then $R_1$, $R_2$ and $R_3$ are independently selected from a hydrogen atom and an alkyl group, and a phenyl group such that $R_1$, $R_2$ and $R_3$ are not all hydrogen atoms; and wherein if Z is an oxygen atom and Y is a hydroxyl group, then (iv) at least one of $R_1$, $R_2$ and $R_3$ is a phenyl group and the other substituents are selected from the group consisting of a hydrogen atom, an alkyl group and a phenyl group, (v) $R_1$ and $R_3$ are selected from the group consisting of an alkyl group and a phenyl group and $R_2$ is selected from the group consisting of a hydrogen atom, an alkyl group and a phenyl group, or (vi) all three of $R_1$, $R_2$ and $R_3$ are alkyl groups.

* * * * *